US008644524B1

(12) United States Patent
Malachowsky

(10) Patent No.: US 8,644,524 B1
(45) Date of Patent: Feb. 4, 2014

(54) NOISE REDUCTION IN ELECTRONIC SYSTEMS

(75) Inventor: Chris Alan Malachowsky, Los Altos Hills, CA (US)

(73) Assignee: Nvidia Corporation, Santa Clara, CA (US)

( * ) Notice: Subject to any disclaimer, the term of this patent is extended or adjusted under 35 U.S.C. 154(b) by 1352 days.

(21) Appl. No.: 11/551,164

(22) Filed: Oct. 19, 2006

(51) Int. Cl.
*G01K 11/16* (2006.01)
*H03B 29/00* (2006.01)
*A61F 11/06* (2006.01)

(52) U.S. Cl.
USPC ....................................... 381/71.9; 381/71.13

(58) Field of Classification Search
USPC ............................ 381/71.1–71.6, 71.9, 71.14
See application file for complete search history.

(56) References Cited

U.S. PATENT DOCUMENTS

| | | | | |
|---|---|---|---|---|
| 4,506,380 | A * | 3/1985 | Matsui | 381/71.9 |
| 5,412,735 | A * | 5/1995 | Engebretson et al. | 381/71.13 |
| 5,452,362 | A * | 9/1995 | Burward-Hoy | 381/71.5 |
| 2003/0123675 | A1* | 7/2003 | Culman et al. | 381/71.3 |
| 2006/0204015 | A1* | 9/2006 | Ip et al. | 381/71.1 |

* cited by examiner

*Primary Examiner* — Ping Lee
(74) *Attorney, Agent, or Firm* — Patterson + Sheridan, L.L.P.

(57) ABSTRACT

Methods and systems for reducing noise relating to an electronic system are disclosed. The methods and systems determine a noise signature, which characterizes a targeted noise of the electronic system. A cancellation signal is then generated based on this noise signature, so that if the cancellation signal is transmitted, the targeted noise is at least partially reduced.

20 Claims, 5 Drawing Sheets

NOISE REDUCTION IN ELECTRONIC SYSTEMS

BACKGROUND OF THE INVENTION

1. Field of the Invention

Embodiments of the present invention relate generally to audio processing and more specifically to reducing noise in electronic systems.

2. Description of the Related Art

Unless otherwise indicated herein, the approaches described in this section are not prior art to the claims in this application and are not admitted to be prior art by inclusion in this section.

The continued trend in integrated circuit (IC) technology is to increase operating frequencies, data transfer rates, and the average number of transistors per IC, while decreasing IC package sizes. Unfortunately, the rising power density of the ICs results in higher operating temperatures of each IC. As electronic systems include a growing number of ICs to perform ever-increasing complex functions, the aggregated heat dissipation from the ICs can be significant.

A common approach to address the high operating temperatures within these electronic systems is to use fans and air ducts to provide airflow over the heat-generating ICs. Heat is transferred to the air as it flows over the ICs, thus cooling the ICs. Another approach is to transport a reservoir of liquid (e.g., water) to heat spreaders that are connected to the heat-generating ICs. Heat is then transferred to the liquid within the heat spreader, and the liquid circulates back to the reservoir where the heat is dissipated.

However, these cooling approaches generate noises at levels that sometimes can be irritating to the users of the electronic systems. For example, fans typically vibrate due to mass imbalance in their rotors, and air ducts also vibrate when air flows at certain velocities. Such vibration causes sound to be produced. As for a liquid cooling system, sound is mainly generated from operating the pump to circulate the liquid.

As the foregoing illustrates, what is needed in the art is a way to reduce the noises generated by the subsystems used to cool electronic systems.

SUMMARY OF THE INVENTION

Methods and systems for reducing noise relating to an electronic system are disclosed. The methods and systems determine a noise signature, which characterizes a noise produced by the electronic system. A cancellation signal is then generated based on this noise signature, so that if the cancellation signal is transmitted, the produced noise is at least partially reduced.

One advantage of the disclosed methods and systems is that they ameliorate the undesirable side effects of deploying the various cooling solutions in electronic systems by reducing the noise produced by these cooling solutions.

BRIEF DESCRIPTION OF THE DRAWINGS

So that the manner in which the above recited features of the present invention can be understood in detail, a more particular description of the invention, briefly summarized above, may be had by reference to embodiments, some of which are illustrated in the appended drawings. It is to be noted, however, that the appended drawings illustrate only typical embodiments of this invention and are therefore not to be considered limiting of its scope, for the invention may admit to other equally effective embodiments.

DETAILED DESCRIPTION

Methods and systems for reducing noise in electronic systems are described. In the following description, for the purposes of explanation, numerous specific details are set forth in order to provide a thorough understanding of the present invention. It will be apparent, however, to one skilled in the art that the present invention may be practiced without these specific details.

Throughout this disclosure, a "media processing unit" refers to a processing unit that mainly handles multimedia data. Some examples of a media processing unit include, without limitation, a graphics processing unit, an audio processing unit, and a signal processing unit. An "electronic system" broadly refers to any system that includes electronic components. Some examples of an electronic system include, without limitation, a computer, a server, a portal device, a multimedia player, a set-top box, and a game console.

Figure 1:
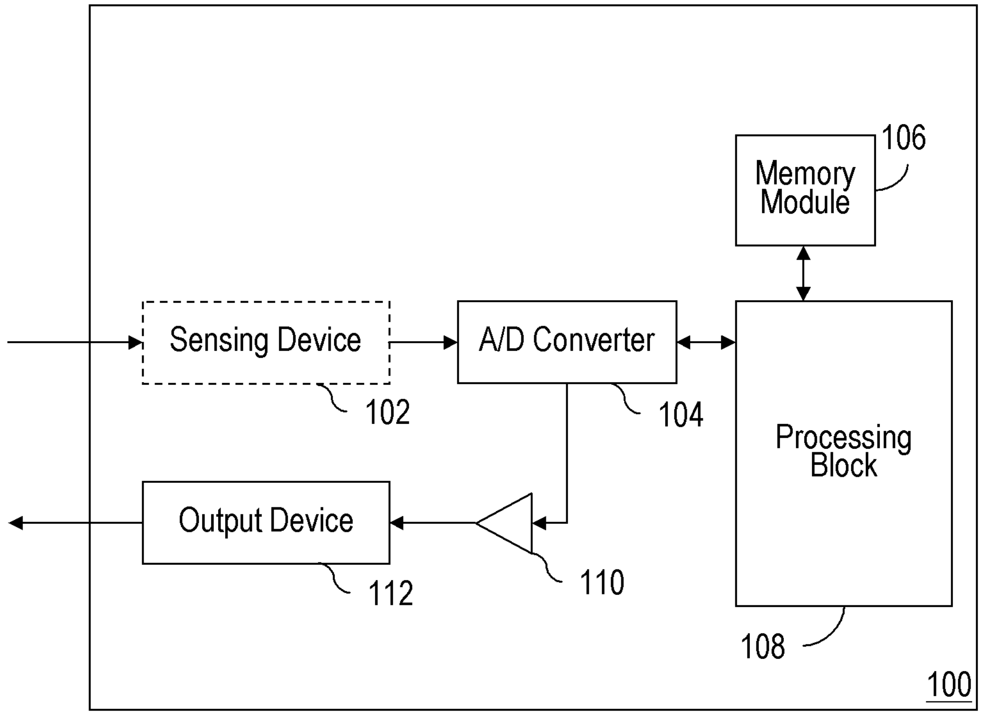
FIG. 1 is a simplified block diagram of a noise reduction subsystem, according to one embodiment of the present invention.

FIG. 1 is a simplified block diagram of a noise reduction subsystem, 100, according to one embodiment of the present invention. Specifically, noise reduction subsystem 100 includes analog/digital ("ND") converter 104, memory module 106, processing block 108, amplifier 110, and at least one output device 112. Depending on the type of noise reduction process employed by noise reduction subsystem 100, noise reduction subsystem 100 may further include at least one sensing device 102. The different noise reduction processes will be discussed in subsequent paragraphs. Sensing device 102 is mainly responsible for capturing sound waves produced by noise sources that are within its detection range and converting the captured sound waves into analog signals. An example of sensing device 102 is a microphone. A/D converter 104 converts analog signals into digital signals and vice versa. Memory module 106 stores instructions for processing block 108, data, certain noise signatures, and intermediary values resulting from the processing performed by processing block 108. Memory module 106 is however not required to be dedicated to computations performed by processing block 108. Processing block 108 mainly performs noise reduction algorithms to compute cancellation signals that can be used to remove or dampen the various noise signals. Some examples of processing block 108 include, without limitation, a microprocessor, a digital signal processor, an embedded processor, analog circuitry, and non-processor based dedicated hardware. Amplifier 110 generates electrical signals that are based on the computations of processing block 108 to drive output device 112. Output device 112 transmits the cancellation signals. An example of output device 112 is a speaker. Alternatively, each of sensing device 102 and output device 112 can be implemented as a single unit, which may include a logic component that switches between the input and output functionality of this unit. It should be apparent to a person with ordinary skill in the art to physically place output device 112 and sensing device 102 anywhere that processing block 108 is able to reach via either wired or wireless communication channels.

Figure 2A:
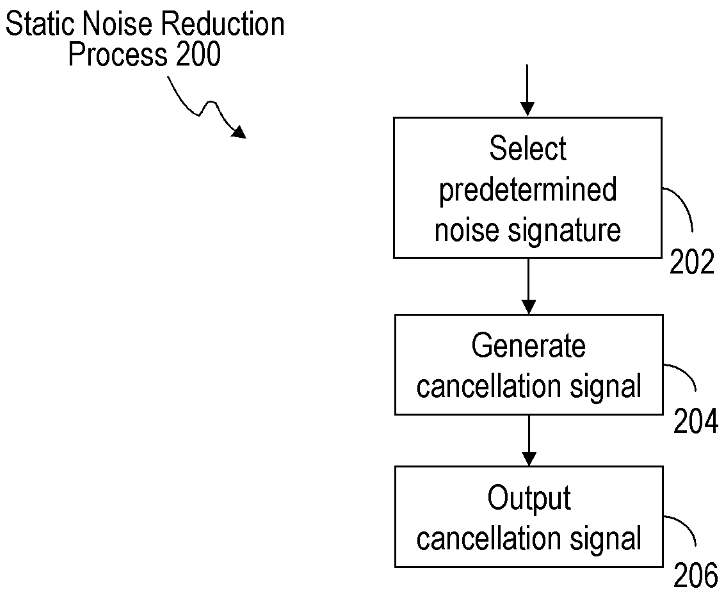
FIG. 2A is a flow chart illustrating a static noise reduction process that a noise reduction subsystem may be configured to implement, according to one embodiment of the present invention.

FIG. 2A is a flow chart illustrating a static noise reduction process, 200, that the static version of noise reduction subsystem 100 may be configured to implement, according to one embodiment of the present invention. In particular, the static version of noise reduction subsystem 100 does not have sensing device 102, because it generates and transmits a cancellation signal based on a predetermined noise signature and does not attempt to identify a noise signature from a noise source. In step 202, a predetermined noise signature representative of a targeted noise, which is associated with an electronic system, is selected. This noise signature can be determined by systems other than noise reduction subsystem 100 in a controlled setting, such as a laboratory. For instance, engineers could simulate the environment in which the electronic system would operate. Then different testing schemes can be devised to capture and characterize the various noise signals introduced by the electronic system or the subsystems of the electronic system. Some examples of the testing schemes are described in the subsequent paragraphs. Generally, the testing schemes may change from time to time to establish different predetermined noise signatures.

In one implementation, a testing scheme may include steps of decomposing a predetermined noise signature into its constituent components. For example, a noise signature representative of the noise resulting from the operations of the entire electronic system may be further dissected into individual components, each of which corresponds to a non-negligible source of noise within the electronic system and having a distinct noise signature. In another implementation, a testing scheme may also include steps of varying the operating conditions of the electronic system. Some examples include, without limitation, varying fan speed of the cooling subsystem in the electronic system, varying the clock speed of the processing units in the electronic system, accessing different peripheral devices external to the electronic system, and executing software programs with varying levels of complexity on the electronic system.

In one implementation of the static version of noise reduction subsystem 100, the predetermined noise signatures are stored in memory module 106. The selection of a particular predetermined noise signature may be triggered by the occurrence of an operating condition. As an illustration, suppose three predetermined noise signatures, A, B, and C, have been determined, each of which corresponds to a fan speed, speed (A), speed (B), and speed (C), respectively. Suppose further that the processing unit in the electronic system tracks the fan speed and communicates such information to noise reduction subsystem 100. Thus, when the fan speed of the electronic system is at speed (B), the processing unit informs noise reduction subsystem 100 and causes the predetermined noise signature 8 in memory module 106 to be selected and retrieved by processing block 108. In an alternative embodiment, the cooling subsystem of the electronic system, as opposed to the processing unit, tracks and communicates the fan speed to noise reduction subsystem 100. It should be apparent to one with ordinary skill in the art to recognize that the selection mechanism discussed above applies to other operating conditions of the electronic system.

After having selected the predetermined noise signature, a cancellation signal is generated in step 204. This cancellation signal has approximately the same amplitude and the opposite polarity to the noise signature. In one implementation, processing block 108 is programmed to generate the cancellation signal based on the predetermined noise signature stored in memory module 106. After processing block 108 establishes the digital representation of the cancellation signal, the digital cancellation signal is converted to an analog signal by A/D converter 104. Amplifier 110 then generates appropriate electric signals based on the analog information to drive output device 112, so that output device 112 can transmit the cancellation signal in step 206. In one implementation, output device 112 continues to transmit the cancellation signal for as long as the electronic system is up and running. Alternatively, similar to the noise signature, the cancellation signal may be pre-computed by systems other than noise reduction subsystem 100. In other words, instead of generating the cancellation signal in step 204, noise reduction subsystem 100 can select the pre-computed cancellation signal corresponding to the noise signal for output.

Figure 2B:
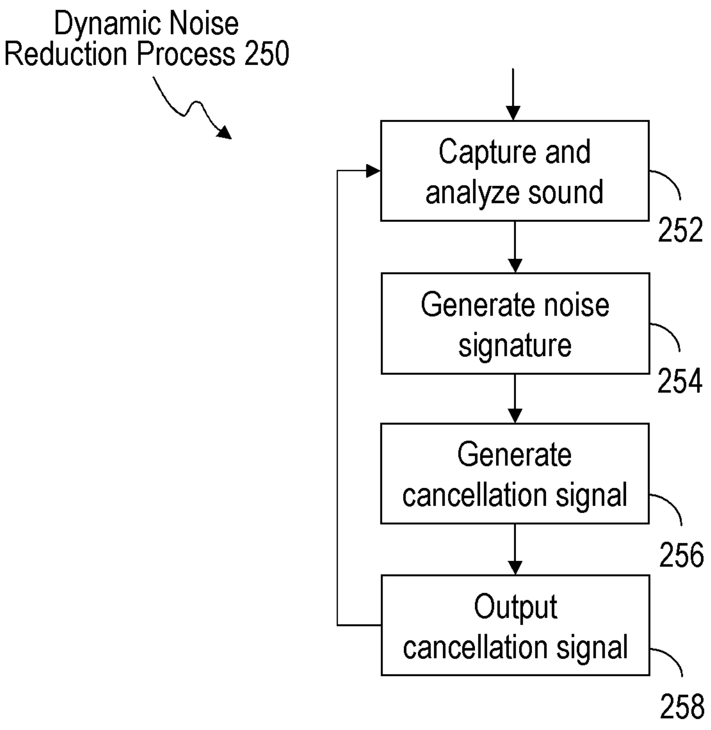
FIG. 2B is a flow chart illustrating a dynamic noise reduction process that a noise reduction subsystem may be configured to implement, according to an alternative embodiment of the present invention.

FIG. 2B is a flow chart illustrating a dynamic noise reduction process, 250, that the dynamic version of noise reduction subsystem 100 of FIG. 1 may be configured to implement, according to another embodiment of the present invention. The dynamic version of noise reduction subsystem 100 includes sensing device 102. Specifically, sensing device 102 captures sound waves, and processing block 108 analyzes the captured information in step 252. Based on this captured information, processing block 108 generates the noise signature in step 254 and generates a corresponding cancellation signal in step 256 for output device 112 to transmit in step 258. The process then loops back to step 252. By capturing and analyzing sound waves, the dynamic version of noise reduction subsystem 100 is able to dynamically and iteratively adjust the generated noise signature and also the corresponding cancellation signal to improve the quality of noise reduction. It should be apparent to one with ordinary skill in the art to implement noise reduction subsystem 100 described above in the analog domain. For example, specific analog waveform generation circuits can be implemented to output the pre-computed cancellation signals. Also, such an analog system does not need to employ ND converter 104 and memory module 106 shown in FIG. 1.

Figure 3A:
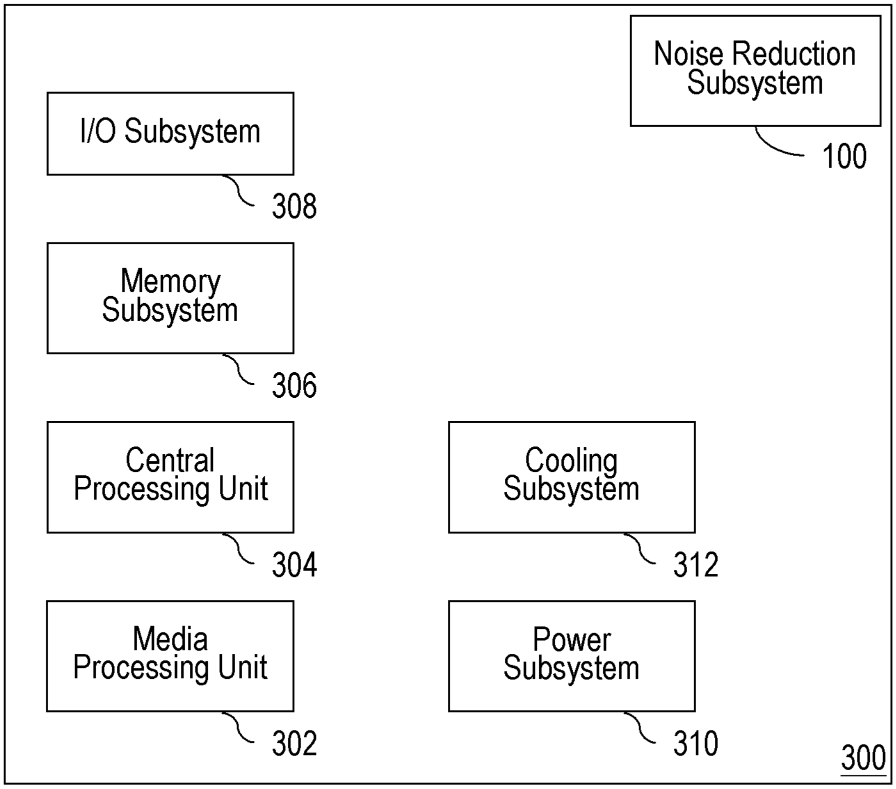
FIG. 3A is a conceptual diagram of a noise reduction subsystem residing inside the chassis of an electronic system, according to one embodiment of the present invention.

The physical locations of noise reduction subsystem 100 of FIG. 1 vary depending on the type of noise the subsystem is configured to address. FIG. 3A is a conceptual diagram of noise reduction subsystem 100 residing inside the chassis of electronic system 300, according to one embodiment of the present invention. In this implementation, noise reduction subsystem 100 is configured to target the noise inside the chassis of electronic system 300. Thus, noise reduction subsystem 100 is placed near the edge of electronic system 300 and away from media processing unit 302, central processing unit 304, memory subsystem 306, input/output subsystem 308, power subsystem 310, and cooling subsystem 312. Such placement allows the dynamic version of noise reduction subsystem 100 to capture the aggregated sound inside the chassis and generate a cancellation signal by following the aforementioned dynamic noise reduction process 250 to counter such noise. Alternatively, if the static version of noise reduction subsystem 100 following the aforementioned static noise reduction process 200 is utilized, then the aggregated sound may be captured and analyzed in a controlled setting so that a corresponding predetermined noise signature can be established. For example, one way to determine this aggregated sound may be to calculate the difference between the sound inside the chassis when electronic system 300 is powered on and operating and the sound inside the chassis when electronic system 300 is powered off. Then, the noise signature is stored in memory module 106 for processing block 108 to process.

Figure 3B:
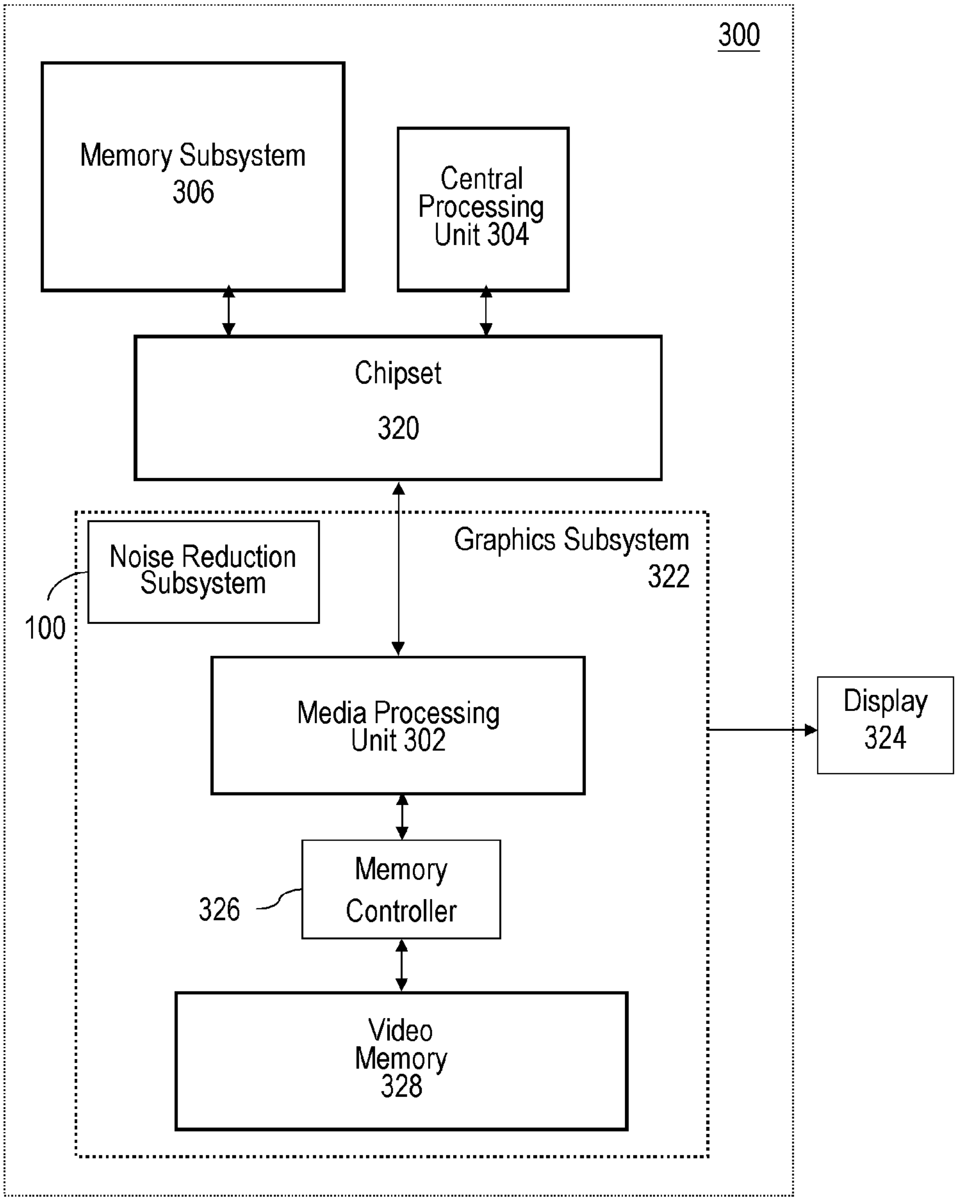
FIG. 3B is a conceptual diagram of a noise reduction subsystem integrated in a standard subsystem in an electronic system, according to one embodiment of the present invention.

In another implementation, noise reduction subsystem 100 of FIG. 1 can be configured to target the specific noise generated by a particular component in electronic system 300. For example, noise reduction subsystem 100 can reside near media processing unit 302 to cancel the noise generated by the cooling subsystem used to cool media processing unit 302. FIG. 3B is a conceptual diagram of noise reduction subsystem 100 integrated in a standard subsystem in electronic system 300, such as graphics subsystem 322, according to one embodiment of the present invention. One example of graphics subsystem 322 is a graphics card. Specifically, graphics subsystem 322 includes, without limitation, media processing unit 302, memory controller 326, and video memory 328. Graphics subsystem 322 further couples to central processing unit 304 and memory subsystem 306 via chipset 320. Graphics subsystem 322 also couples to display device 324. One way to establish the noise produced by media processing unit 302 is to directly measure and estimate the sound generated by the cooling subsystem used to cool media processing unit 302. For the static version of noise reduction subsystem 100 following static noise reduction process 200, this direct measurement and estimation may be conducted with media processing unit 302 or graphics subsystem 322 operating in a standalone fashion to establish a predetermined noise signature that can be stored in memory module 106 of FIG. 1. On the other hand, if dynamic noise reduction process 250 is followed, then the dynamic version of noise reduction subsystem 100 may be used to iteratively evaluate the noise signal produced by media processing unit 302 during operation and generate the appropriate cancellation signal. Similarly, noise reduction subsystem 100 can also reside near any other noise-generating components in electronic system 300, such as, without limitation, power subsystem 310 or cooling subsystem 312 of FIG. 3A.

Figure 3C:
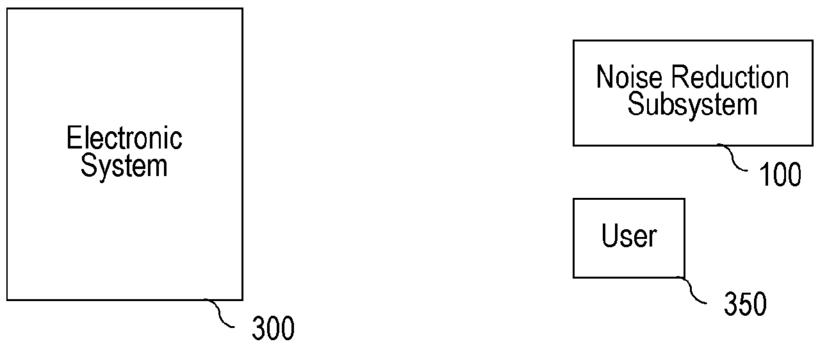
FIG. 3C is a conceptual diagram of a noise reduction subsystem residing near a user of an electronic system, according to one embodiment of the present invention.

FIG. 3C is a conceptual diagram of noise reduction subsystem 100 of FIG. 1 residing near user 350 of electronic system 300, according to one embodiment of the present invention. Specifically, noise reduction subsystem 100 in this implementation is configured to target the aggregated noise generated by electronic system 300 in a certain environment. This aggregated noise includes at least the internal noise and the chassis noise of electronic system 300 and the ambient noise of this environment. Thus, by placing noise reduction subsystem 100 near user 350, the noise that is perceivable by the user can be removed or dampened. Noise reduction subsystem 100 may embed in a number of items including, without limitation, a peripheral device of electronic system 300, such as a desktop/desk side module, a keyboard, a mouse, or a remote control, a portal device, such as a cellular phone, a personal digital assistant, or a multimedia player, a piece of furniture, a display device, or a game console. One way to determine this aggregated noise may be to separately determine the noise produced by electronic system 300 and the ambient noise of the environment and then combine the two types of noises.

Figure 3D:
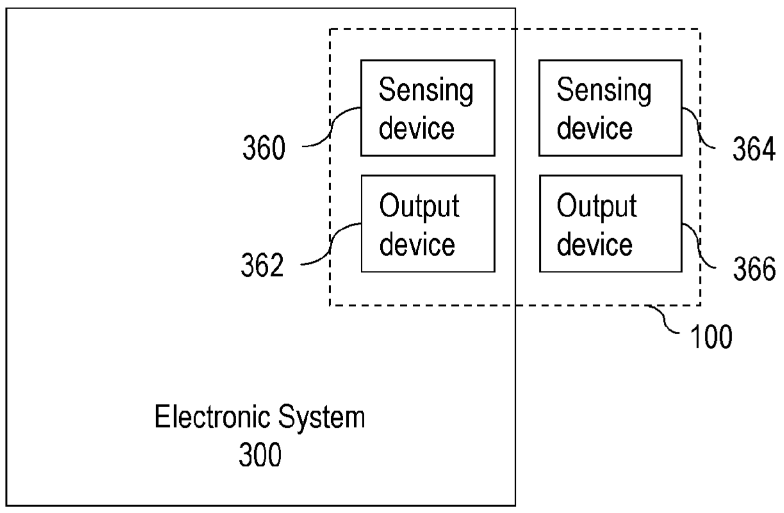
FIG. 3D is a conceptual diagram of a noise reduction subsystem with at least one sensing device residing inside of an electronic system and at least another sensing device residing outside of the same electronic system, according to one embodiment of the present invention.

FIG. 3D is a conceptual diagram of noise reduction subsystem 100 of FIG. 1 with at least one sensing device residing inside of electronic system 300 and at least another sensing device residing outside of electronic system 300, according to one embodiment of the present invention. Specifically, noise reduction subsystem 100 in this implementation is configured to target both the noise generated inside the chassis of electronic system 300 and also the noise experienced by the user that is "external" to electronic system 300. This external noise includes both the noise generated by the chassis vibrations as well as the ambient noise of the user's environment. Sensing device 360 and sensing device 364 are thus responsible for capturing the aggregated sound inside and outside the chassis of electronic system 300, respectively. Suppose the aggregate sound inside the chassis is considered as the internal noise, and the aggregated sound outside the chassis represents an approximate sum of the internal noise and the noise external to electronic system 300. Output device 362 may generate a cancellation signal to offset the internal noise. Moreover, processing block 108 of noise reduction subsystem 100 subtracts the internal noise from the aggregate noise outside the chassis of electronic system 300 to obtain the approximate noise external to electronic to electronic system 300. With this approximation, a corresponding noise signature and a cancellation signal are generated, and output device 366 transmits the cancellation signal for the external noise.

In an alternative embodiment, sensing device 360 and output device 362 belong to an internal noise reduction subsystem, and sensing device 364 and output device 366 belong to an external noise reduction subsystem. These two subsystems reside inside and outside the chassis of electronic system 300, respectively. In one implementation, the external noise reduction subsystem resides near the user of electronic system 300. Furthermore, since these subsystems reside in two different locations, the subsystems further include communication links to exchange relevant noise information. It should be apparent to a person of ordinary skills in the art to utilize any number of noise reduction subsystems inside or outside of electronic system 300, generate and manipulate various noise signatures, and target any number of types of noises without exceeding the scope of the claimed invention.

The above description illustrates various embodiments of the present invention along with examples of how aspects of the present invention may be implemented. The above examples, embodiments, and drawings should not be deemed to be the only embodiments, and are presented to illustrate the flexibility and advantages of the present invention as defined by the following claims.

I claim:

1. An electronic system, comprising:

a cooling subsystem;

a processing unit configured to monitor an operating characteristic of the cooling subsystem;

a media processing unit that is cooled by the cooling subsystem; and a first noise reduction subsystem configured to:

receive data associated with the operating characteristic from the processing unit, select a first noise signature that characterizes a targeted noise of the cooling subsystem based on the data received from the processing unit, wherein the first noise signature is one of a plurality of predefined noise signatures stored in the noise reduction subsystem; and generate a first cancellation signal derived from the first noise signature, wherein the first cancellation signal at least partially offsets the noise generated by the cooling subsystem, wherein the first noise signature has been decomposed into constituent components, each with a corresponding component noise signature.

2. The electronic system of claim 1, wherein the first noise reduction subsystem comprises:

a digital signal processor to select the first noise signature and generate the first cancellation signal; and a first output device to convert the first cancellation signal into sound.

3. The electronic system of claim 2, wherein the noise reduction subsystem further comprises:

a memory module configured to store the plurality of predefined noise signatures, wherein a system other than the first noise reduction subsystem determines the plurality of predefined noise signatures.

4. The electronic system of claim 3, wherein the system other than the first noise reduction subsystem further varies operating conditions of the cooling subsystem to determine the first noise signature.

5. The electronic system of claim 4, wherein the first noise reduction subsystem selects the first noise signature stored in a memory module upon an occurrence of one of the operating conditions.

6. The electronic system of claim 2, wherein a second noise reduction subsystem resides outside of the electronic system and near a user of the electronic system to convert a second cancellation signal into sound to at least partially offset an external noise perceivable by the user.

7. The electronic system of claim 6, further comprising:

a sensing device residing outside the chassis of the electronic system to capture an external noise of the electronic system; and a second output device to convert the second cancellation signal into sound, wherein the digital signal processor generates a second cancellation signal for the second output device to at least partially offset the external noise.

8. The electronic system of claim 7, wherein the sensing device is included in a keyboard or a mouse.

9. The electronic system of claim 1, wherein each constituent component corresponds to a non-negligible source of noise within the electronic system and having a distinct noise signature.

10. The electronic system of claim 1, wherein the first noise reduction subsystem is further configured to:

calculate a difference between an aggregate noise outside the electronic system and the targeted noise of the cooling subsystem to obtain the approximate noise external to the electronic system;

generate a second noise signature corresponding to the difference; and generate a second cancellation signature corresponding to the second noise signature.

11. A method for reducing noise produced by an electronic system, comprising:

receiving data associated with an operating characteristic of a cooling subsystem from a processing unit of the electronic system, wherein the cooling subsystem cools a media processing unit;

selecting a first noise signature that characterizes a targeted noise of the cooling subsystem, wherein the first noise signature is one of a plurality of predefined noise signatures stored in a noise reduction subsystem;

generating, in the first noise reduction subsystem, a first cancellation signal based on the first noise signature; and converting the first cancellation signal to sound to at least partially offset the targeted noise; and decomposing the first noise signature into constituent components, each with a corresponding component noise signature.

12. The method of claim 11, further comprising:

capturing a sound wave;

converting the sound wave into a digital signal; and analyzing the digital signal to generate a second noise signature.

13. The method of claim 11, further comprising:

devising a test scheme to determine the targeted noise and identify the first noise signature in a controlled setting; and utilizing the first noise signature until the test scheme is modified.

14. The method of claim 13, further comprising varying operating conditions of the cooling subsystem to determine the plurality of noise signatures.

15. The method of claim 14, further comprising selecting the first noise signature to generate the cancellation signal upon an occurrence of one of the operating conditions as indicated by the data received from the processing unit.

16. The method of claim 11, further comprising converting the first cancellation signal to sound near the cooling subsystem to at least partially offset a noise, wherein the first cancellation signal is derived from a particular noise signature associated with the cooling subsystem.

17. The method of claim 11, further comprising converting a second cancellation signal to sound outside of the electronic system and near a user of the electronic system to at least partially offset an external noise perceivable by the user.

18. The method of claim 11, further comprising:

capturing an external noise of the electronic system;

generating a second cancellation signal derived from the external noise; and converting the second cancellation signal to sound outside of the electronic system to at least partially offset the external noise.

19. The method of claim 11, wherein each constituent component corresponds to a non-negligible source of noise within the electronic system and having a distinct noise signature.

20. The method of claim 11, further comprising:

calculating a difference between an aggregate noise outside the electronic system and the targeted noise of the cooling subsystem to obtain the approximate noise external to the electronic system;

generating a second noise signature corresponding to the difference; and generating a second cancellation signature corresponding to the second noise signature.

* * * * *